United States Patent
Sutton et al.

[11] Patent Number: 5,955,108
[45] Date of Patent: Sep. 21, 1999

[54] CROSS-LINKED MICROPARTICLES AND THEIR USE AS THERAPEUTIC VEHICLES

[75] Inventors: Andrew Derek Sutton, Grantham; Richard Alan Johnson, Nottingham, both of United Kingdom

[73] Assignee: Quadrant Healthcare (UK) Limited, United Kingdom

[21] Appl. No.: 08/876,489

[22] Filed: Jun. 16, 1997

Related U.S. Application Data

[63] Continuation-in-part of application No. PCT/GB95/02925, Dec. 14, 1995.

[51] Int. Cl.$^6$ .............................. A61K 9/14; A61K 9/50
[52] U.S. Cl. ...................... 424/489; 424/423; 424/426; 424/490; 514/937; 514/952
[58] Field of Search ................... 424/489, 490, 424/423, 426

[56] References Cited

U.S. PATENT DOCUMENTS

| | | | |
|---|---|---|---|
| 3,565,559 | 2/1971 | Sato et al. | 424/37 |
| 3,960,583 | 6/1976 | Netting et al. | 106/122 |
| 5,145,684 | 9/1992 | Liversidge et al. | 424/489 |
| 5,663,198 | 9/1997 | Reul et al. | 514/471 |

FOREIGN PATENT DOCUMENTS

| | | |
|---|---|---|
| 0 494 417 A2 | 7/1992 | European Pat. Off. . |
| 0 681 843 A2 | 11/1995 | European Pat. Off. . |
| WO 91/12823 | 9/1991 | WIPO . |
| WO 92/18164 | 10/1992 | WIPO . |
| WO 93/17713 | 9/1993 | WIPO . |
| WO 94/08627 | 4/1994 | WIPO . |
| WO 95/31479 | 11/1995 | WIPO . |
| WO 96/09814 | 4/1996 | WIPO . |
| WO 96/18388 | 6/1996 | WIPO . |

*Primary Examiner*—Thurman K. Page
*Assistant Examiner*—James M. Spear
*Attorney, Agent, or Firm*—Sterne, Kessler, Goldstein & Fox P.L.L.C.

[57] ABSTRACT

A sterile powder comprising microparticles, 0.1 to 50 $\mu$m in diameter, obtainable by spray-drying and cross-linking a water-soluble material having free functional groups, is characterized in that the microparticles are hydrophilic, can be reconstituted in water to give a monodisperse suspension, and have retained said groups available for derivatization. The particles are linked to drugs or other functional molecules, and used as vehicles in therapy.

18 Claims, No Drawings

CROSS-LINKED MICROPARTICLES AND THEIR USE AS THERAPEUTIC VEHICLES

CROSS-REFERENCE TO RELATED APPLICATION

This Application is a continuation-in-part of International Patent Application No. PCT/GB95/02925, filed Dec. 14, 1995.

FIELD OF THE INVENTION

This invention relates to cross-linked microparticles and to their use as therapeutic vehicles.

BACKGROUND OF THE INVENTION

Microparticulate carrier systems are increasingly attracting attention for use in the parenteral delivery of therapeutic and diagnostics agents. A plethora of microparticle technology systems and chemistries has been proffered as vehicles to deliver agents subcutaneously, intravenously and intra-arterially. There are several key aspects to the "ideal vehicle". These include size, size distribution, payload, rate of biodegradation, ease of use, release kinetics and scalable reproducible production. Individual aspects of this "ideal vehicle" have been successfully addressed by others, notably drug payload, rate of biodegradation and, in part, size and size distribution.

Known vehicles have been manufactured by various techniques, largely solvent and emulsion-based. A disadvantage of these methods is that control of the key elements of the vehicle was attempted within one or two steps of the production. Thus, size, size distribution, payload and rate of biodegradation were all imparted on the product in a single, dynamic environment, typified by single and double emulsion systems or solvent evaporation techniques. Typically, for emulsion processes, the solution of drug, polymer and surface-modifying agents has been mixed with an insoluble solvent, emulsified, heated or stabilised to fix the particles, and then cleansed to remove oils or solvent incompatible with parenteral use.

The reaction vessel in emulsion or solvent evaporation systems is a principal characteristic of the prior art techniques. Within this vessel, the control of the microparticle morphology is achieved by balancing the interfacial forces of oil and water components, the interaction of solute at the interface, the balance between agitation, heat and shell formation and, of course, the incorporation of active within the polymer matrix. However, such technologies are largely incompatible with large-scale pharmaceutical manufacture required for a parenteral agent.

Almost without exception, the control of size and size distribution of known microparticles was vastly inferior to the size control attained by the spray-drying techniques described in the PCT publications WO-A-9112823, WO-A-9218164 and WO-A-9408627, in the production of microparticles for use in echo-contrast imaging and other potential parenteral uses. The acute toxicity of intravenous microparticles is largely associated with capillary blockage in the pulmonary circulation, concurrent decrease in the pulmonary venous pressure and loss of compliance. The relationship between particle size and LD toxicity is well recorded. Our own data show the precipitous elevation in toxicity of iv particles, with a mean size in excess of 6 $\mu$m, the notional capillary size in lung tissue for non-deformable microcapsules.

Typically, the larger the mean size of the capsules, the significantly broader their size distribution, and the range of microparticle sizes can span two orders of magnitude. For therapeutic use, such as chemo-embolisation, the prospect of injecting a microparticle preparation containing particles ranging in size from 5–100 $\mu$m is largely inconsistent with the concept of highly regionalised targeted delivery. At the upper end, there is the prospect of embolising major vessels up to and above 100 $\mu$m in diameter, with the attendant risk of necrosing large perfusion territories; at the smaller end of the range, what essentially amounts to systemic distribution becomes possible.

The mechanism by which sustained release has previously been most commonly achieved in microparticle systems has been the control of matrix erosion and release to the surrounding medium of embedded or imbibed active agents. The active agents have either been incorporated at the time of particle production or imbibed into the matrix following fixation or stabilisation.

The incorporation of drugs into the matrix of the known microcapsules required heating in the presence of water and, inevitably, oxygen. This would almost certainly lead to adulteration of the drug by oxidative damage or uncontrolled cross-linking to the vehicle. In those cases where chemical stabilisation is used, the potential loss of active would be even worse.

Another mechanism of slowing or modifying release rates of drugs from soluble polymeric carriers has been to link the active agents via covalent linkages to the soluble polymer. In general, this has not been applied to microparticulate systems where drugs, ligands or antibodies are linked to particulate carriers.

The main impediment to linking active agents to prior art microparticles, is the latter's relative hydrophobicity. Since many of the chemical reactions required to achieve linkage are carried out in aqueous medium, such hydrophobic microparticles are almost impossible to derivatise. Where previous workers have produced hydrophilic microcapsules, they required complex formation in the presence of hydrophilic polymer, in an emulsion process.

The rate of biodegradation of microcapsules is determined largely by the extent of cross-linking. In the prior art systems, changes in cross-linking have detrimental effects upon drug loading and the ability subsequently to formulate the microparticles. Little effort was expended in attempting to manipulate this parameter to control the rate of biodegradation and drug release.

Microparticles of the prior art have required significant amounts of surfactants or sonication to achieve monodispersed suspension in aqueous media. Even when reconstituted, the microparticles have a propensity to agglomerate and are thus difficult to administer through hypodermic syringes.

It is known to use carrier materials in order to target cytotoxic drugs to the site of action. Typically, microparticles or other such materials comprise a matrix in which the drug is entrapped.

SUMMARY OF THE INVENTION

This invention is based on the discovery that microparticles of the type described in the PCT publications WO-A-9112823, WO-A-9218164 and WO-A-9408627, having good particle characteristics, can retain, even after crosslinking, their hydrophilic properties and the ability to be reconstituted in water to give a monodisperse suspension. Further, functional groups such as carboxyl, amine, hydroxyl or sulfhydryl groups in the starting material are retained, and are available for derivatisation.

According to the present invention, a sterile powder comprises smooth, spherical microparticles, 0.1 to 50 μm in diameter, of cross-linked materials, the microparticles being hydrophilic and capable of reconstitution in water to give a mono-disperse suspension, and which additionally comprises a physiologically or diagnostically-active component linked directly or indirectly to microparticles via free functional, e.g. amine, hydroxyl, carboxyl or sulfhydryl, groups thereon.

DESCRIPTION OF THE INVENTION

This invention preferably utilises a microparticle production technique of the type described in the PCT publications, supra (the contents of which are incorporated herein by reference), in which there is tight control over size, size distribution, payload, rate of biodegradation and release kinetics, providing ease of use and scalable production. The microparticles of this invention may be tailored at will to suit the application whilst retaining, in all cases, the ability to produce the loaded vehicle at scale to high levels of pharmaceutical practice and always with the same level of control. In addition to control of size, independent control, in individual steps, is possible for size distribution; rate of fixation or, reciprocally, rate of biodegradation; drug loading; and formulation and finishing. As previously disclosed in the PCT publications, supra, the Applicants have a fully scaled process which can produce microparticles of the nature specified. The process may be operated to pharmaceutical standards without the ingress of foreign particulates that would most certainly preclude parenteral use of microparticles produced by many of the prior art processes.

The present invention relates to the production of microparticle preparations for intravenous, intraarterial and ex vivo use. Intravenous particle suspensions, on reconstitution in diluent, preferably contain less than 5% by volume of particles larger than 6 μm. Furthermore, the size distribution is near Gaussian in shape, with some 50% of particles lying within a range of 5 μm, preferably 3 μm, more preferably 2 μm and most preferably 1.2 μm. A desirable distribution has 80% of particles in a range of 3 μm. (All distributions quoted on a volume or mass basis). One preferred embodiment of the invention is powders wherein 95% of the particles are smaller than 6 μm, and 80% of the particles are in the range of 1 to 6 μm, especially for iv administration. Another preferred embodiment is powders wherein 90% of the particles are smaller than 20 μm, and less than 5% by volume are smaller than 6 μm, especially for intraarterial administration.

For larger particle systems, by utilising a combination of highly controlled spray-drying and a subsequent fractionation step, it is possible to produce microparticles of sufficient size and tight size distribution such that, following intraarterial administration, systemic release is eliminated and only vessels smaller than 20 μm become embolised.

In one embodiment of the current invention, we have incorporated active within the feedstock for spray-drying and subsequently stabilised the particle. The advantage we have gained is vastly superior control of morphology and payload over previous methodologies.

The process used in this invention may involve the deposition of wall material and drug into dry powder state, with negligible water content, capable of being reconstituted to the original soluble components.

The microcapsules can be cross-linked by various processes, including the use of heat or chemical means. The adjustment of the degree of fixation results in the subsequent degree to which the microcapsules will dissolve in an appropriate medium. Moreover, any active compounds bound or encapsulated within the microcapsules will be released at this point of dissolution. In addition, the degree to which the microcapsules are fixed is also reflected in the degree to which they can be digested enzymatically. The greater the degree of fixation, the greater the resistance of the microcapsules to enzymic digestion.

In this invention, cross-linking can be used to control the release rates of active agents. For example, in one embodiment, the extent of cross-linking, and hence the rate of degradation, is "set" prior to attachment of the active. The active ligand may then be attached, and shows a controlled release profile determined by the extent to which the matrix was cross-linked. This has the advantage that a steady rate of release is observed without the well-known "burst" effect.

A further aspect of this invention is the manipulation of cross-linking. Potential levels of derivatisable groups and temperature/time required for cross-linking may be controlled by the incorporation of additives which alter these parameters. Inclusion of amino-acids such as lysine or polylysine, glutamate or polyglutamate, phenylalanine and tyrosine into the feedstock can have the effect of increasing or decreasing the biodegradation rate of the final microparticle preparation. Additionally, the incorporation of these additives can significantly increase the number of potential groups to which active agents, or ligands, may be attached. Furthermore, incorporation of these additives can reduce the time/temperature at which microparticle stabilisation occurs during heating of the soluble microparticles formed after spray-drying.

Accordingly, therefore, while the present invention provides microparticles that are especially suitable for delivery to defined sites, owing to their narrow particle size distribution, a combination of desirable features has been found that make the microparticles especially useful.

It has been discovered that microcapsules manufactured using the techniques described, have several superior properties over the prior art microparticles with regard to the ability to handle, derivatise and formulate the microparticles. Thus, for example, the Applicants' technology enables the production of microparticles which apparently retain a substantial degree of secondary structure, and thus hydrophilicity instead of being denatured, and rendered insoluble, with hidden functional groups, as in the prior art. In particular, the microparticles:

(i) possess significant levels of amine, hydroxyl or carboxyl groups, or a combination thereof, for derivatisation, (ii) are highly hydrophilic with full access by aqueous media for the derivatisation of the active groups, (iii) may be manipulated in dry or wet state to yield dry final formulations that do not require surfactants or sonication to yield monodispersed suspensions of particles, (iv) biodegrade and release active principles at a rate determined by the composition and cross-linking of the shell, (v) may possess sizes ranging from 0.01 μm to 100 μm, and (vi) are retained in circulation in vivo for periods of time (60 min or more), considerably longer than for the more hydrophobic known microparticles, and longer than for liposomes; opsonisation is reduced, and thrombogenic potential minimised.

The particle size is preferably below 4 μm for intravenous administration, and between 8 and 30 μm for intraarterial administration. Especially for larger particles, fractionation is an optional extra step. This particle size range can be expressed such that the ratio of the interquartile range to mean diameter is 0.2 to 0.5.

The microparticles of this invention may be derivatised by conjugation of drugs, ligands, peptides or proteins directly to the carrier using the carboxyl or amine groups of the basic capsules or additives made to the feedstock for spray-drying. For example, conjugation may be achieved using glutaraldehyde, EDCI, terephthaloyl chloride, cyanogen bromide or reductive amination. Alternatively the ligand, drug, protein or peptide may be linked via a biodegradable hydroxy acid linker of the kind disclosed in WO-A-9317713 (Rijksuniversiteit Groningen), the content of which is incorporated by reference.

A further advantage of this invention lies in the ability to formulate and present the product as a dry sterile powder.

Microcapsules of this invention in powder form do not have an absolute requirement for surfactants to ensure a monodispersed suspension on reconstitution. Once reconstituted, they do not agglomerate, and can be administered via syringe.

An aspect of the present invention is a water-compatible system manufactured from biocompatible materials. It could not be anticipated that the microparticles of the current invention could be insolubilised by heating yet retain sufficient secondary structure to remain highly hydrophilic. Evidence of the retention of secondary structure is obtained by examination of the particle isoelectric point (PI) which, at pH 4.5 to 5, is very similar to native albumin. Normally, full denaturation of albumin leads to a significant rise in PI, to a value of 6.5 to 7.0.

Further, digestion of protein microparticles with protease yields peptides which, when compared with digests of the starting soluble protein, show near identical profiles, by HPLC analogues. In addition, acid hydrolysis of protein microparticles and protein starting material show strikingly similar amino-acid content. These two analyses support the observation that the protein in the microparticles is largely native.

The novel particles are hydrophilic and have the potential to circulate for periods in excess of one hour, offering for the first time a biocompatible carrier system showing prolonged circulatory lifetime with a highly specific affinity for ligands. The specificity of the microparticles is "set" during manufacture and imparts a high affinity ligand-binding capability normally associated with chromatography matrices or enzymes. The particles also offer potential for use in contact with biological fluids, for instance in detoxification in extracorporeal systems, bioassays on serum or blood and the separation of blood components prior to reintroduction into the body.

Any of a variety of physiologically- or diagnostically-active components may be used in this invention. Examples of diagnostic agents are given in WO-A-9218164, the contents of which are incorporated herein by reference. Examples of physiologically-active agents, e.g. drugs, are natural factors (which may be recombinant) such as tissue plasminogen activator (TPA), non-steroidal anti-inflammatory agents, including profens and naproxen, fibrinogen, thrombin and cytotoxic agents. Microparticles comprising fibrinogen may be used, to react with endogenous thrombin, to form artificial platelets. In particular, microparticles carrying one or two cytotoxic drugs, or one such drug and a targeting and/or echogenic agent, are useful to overcome tumour resistance to such drugs, including MDR.

Without wishing to be bound by theory, it appears that cytotoxicity is related to the uptake of albumin-based materials by cells of certain tumour types. The microspheres may provide a useful delivery vehicle for intra-cavitary treatment, for example of ovarian carcinoma.

It has been suggested that the expression of the cell membrane efflux pump P-glycoprotein may be responsible for inducible resistance to drugs, including doxorubicin, in a number of human cancers. The novel drug delivery system may have the ability to increase targeting of therapy and may overcome P-glycoprotein-mediated resistance and/or down-regulation of topoisomerase II, perhaps by enhancing intracellular drug retention and overwhelming the mechanisms.

Cytotoxic drugs that may be used in the invention will be readily apparent to one of ordinary skill in the art. Choice will depend on the condition to be treated. Examples include methotrexate, cisplatin, doxorubicin and 5-fluoro-2'-deoxyuridine.

Covalent attachment of the drug to the microcapsule is in contrast to systems that trap drug in the matrix. There may be attachment of a variety of drugs using different cross-linkers (such as EDC) and native binding sites on HSA (OH, $NH_2$, COOH and, for cisplatin, the SH groups). Because of the different binding site available for another active material, e.g. for doxorubicin, cisplatin is a preferred choice for one such material. Different agents may also be chosen because of their different mechanisms of action, or different release rates.

The mechanism of drug loading allows the same microcapsules to be loaded with two (or more) drugs, perhaps using different mechanisms. An example would be doxorubicin and cisplatin loaded on the same microcapsules. Alternatively, microcapsules with different drugs as the pay load could simply be mixed, if cells take up more than one microcapsule.

In either case, the drug-resistant cells may be presented simultaneously with more than one cytotoxic drug. Likewise, the individual tumour cell may be presented with cytotoxic drug simultaneously with another agent such as a cytokine, or a targeting agent such as an antibody. For example, the observed resistance to cisplatin by ovarian carcinomatosis may be overcome by the use of microparticles carrying cisplatin and doxorubicin, by virtue of the much higher cellular cisplatin level and the lethally high doxorubicin level.

Microparticles of this invention are primarily intended for intra-cavitary treatment. For this purpose, they may be administered directly, intraperitoneally or, using relatively small particles, intravenously. They may be formulated with any suitable carrier. The amount to be administered will depend on the nature and degree of the condition being treated and of the patient. It may be such as to give the usual, known dosage of the cytotoxic agent (or other active agent) itself, but higher or lower dosages may be appropriate, as will be readily understood by the skilled man.

The following Examples illustrate the invention.

EXAMPLE 1

This Example illustrates the fixation of soluble microcapsules, to form insoluble or less soluble microcapsules, by cross-linking of the shell material.

HSA microcapsules were produced from a spray-drying feedstock containing 150 ml of 25% ethanol containing 100 mg/ml HSA. The spray-drying conditions used to form the microcapsules are detailed in Table 1, below.

TABLE 1

| Spray Dryer Condition | Setting |
|---|---|
| Inlet Temperature | 220° C. |
| Outlet Temperature-Initial | 85.2° C. |
| Outlet Temperature-Final | 84.0° C. |
| Atomisation Pressure | 7.5 bar |
| Damper Setting | 0.5 |
| Feed Rate | 3.88 g/min |

The spray-drying process produced 17.21 g of microcapsules. Microcapsules from this single production batch were divided into equal sized aliquots and heat-fixed at 175° C. for 45, 55 and 75 minutes respectively. The heat fixation process renders the soluble microcapsules from the spray-drying process insoluble, by cross-linking some of the amino acids within the albumin structure. The three different heat-fixed microcapsules were sized in an aqueous system using a Multisizer II (Coulter Electronics). The microcapsules had a mean size of 3.28±0.6 μm and with 90% of the mass within 2–5 μm.

Prior to binding any active component to the microcapsules, those heat-fixed for 55 minutes were analysed in various ways for their suitability as drug carriers.

Free Thiol Analysis

The free thiol group present in the albumin molecule is very susceptible to modification and hence it can be used as a measure of the state and condition of the albumin. Similarly, it should be present within the microcapsule structure providing the albumin molecule was not disrupted during formation.

Analysis of the free thiol group was carried out by reacting the albumin microcapsules with DTNB, i.e. 5,5'-dithiobis(2-nitrobenzoic acid). If the free thiol is present, it reacts with the DTNB to yield a nitrobenzoic acid derivative that absorbs at 412 nm. The absorbance of a 12 mg/ml suspension of microcapsules at 412 nm was measured. To the suspension, 50 μl of a 20% solution of DTNB in TRIS buffer was added, incubated for 10 min at room temperature and the absorbance measured. The difference between the two absorbances was calculated and from the molecular extinction coefficient of the reaction product, the concentration of the free thiol present in the microcapsules was calculated. The molecular ratio of thiol groups measured in the microcapsules was 0.4785. This compared to a value of 0.5045 for native albumin. This was not a significant difference and it was concluded that the free thiol group was unchanged during microcapsule manufacture.

The microcapsules (both soluble and insoluble) and native albumin were broken down to their constituent amino-acids by vapour phase hydrolysis using concentrated HCl at 120° C. for 24 hr. The samples were then derivatised by the addition of triethylamine in 50% ethanol and followed by triethylamine and PITC in ethanol. The derivatised samples were analysed by HPLC, and the amino-acids detected at a wavelength of 254 nm. The results are shown in Table 2.

TABLE 2

AMINO ACID COMPOSITION OF NATIVE ALBUMIN AND MICROCAPSULES

| Amino Acid | HSA (n = 5) | Soluble Microcapsules (n = 5) | Insoluble Microcapsules (n = 7) |
|---|---|---|---|
| Aspartic Acid | 50.188 ± 2.73 | 57.99 ± 4.13 | 59.23 ± 4.81 |
| Glutamic Acid | 79.31 ± 5.44 | 80.47 ± 2.26 | 85.70 ± 4.04 |
| Serine | 23.21 ± 1.39 | 23.2 ± 1.23 | 20.65 ± 2.44 |
| Glycine | 14.54 ± 0.71 | 15.33 ± 0.38 | 14.93 ± 107 |
| Histidine | 17.34 ± 1.06 | 17.65 ± 1.01 | 16.42 ± 0.85 |
| Threonine | 26.99 ± 1.34 | 27.23 ± 1.56 | 28.39 ± 2.38 |
| Alanine | 63.83 ± 1.34 | 61.45 ± 0.96 | 62.69 ± 1.86 |
| Arginine | 25.18 ± 0.95 | 24.39 ± 1.02 | 23.15 ± 1.55 |
| Proline | 28.36 ± 1.17 | 27.45 ± 2.03 | 25.20 ± 3.05 |
| Tyrosine | 18.37 ± 0.71 | 18.02 ± 0.42 | 16.13 ± 1.38 |
| Valine | 35.54 ± 1.49 | 35.07 ± 1.03 | 37.59 ± 4.53 |
| Methionine | 7.99 ± 0.5 | 7.68 ± 0.42 | 6.24 ± 1.16 |
| Isoleucine | 6.42 ± 0.54 | 6.64 ± 0.57 | 8.96 ± 1.78 |
| Leucine | 63.22 ± 3.48 | 62.13 ± 3.14 | 59.28 ± 4.38 |
| Phenylalanine | 32.00 ± 2.73 | 30.45 ± 2.13 | 30.48 ± 1.92 |
| Lysine | 56.185 ± 2.50 | 53.45 ± 1.62 | 51.68 ± 3.67 |

Unexpectedly, there is no significant difference between the various samples, with only very small losses of amino-acids containing carboxyl, hydroxyl and amide groups after insolubilisation of the microcapsules.

Peptide Analysis

Pepsin digestion of the microcapsules and albumin was performed using a 1 ml acidified solution of microcapsules or albumin, to which was added 20 μl of a 1% pepsin solution. Digestion was carried out at 37° C. for 24 hr followed by a second addition of pepsin and a further incubation at 37° C. until the samples were completely digested. HPLC analysis of the resultant lysates was carried out using an acetonitrile gradient in 0.1% TFA, measuring absorbance at 214 nm.

Trypsin digestion of the microcapsules and albumin was performed on samples initially treated with guanidine-HCl, DTT and iodoacetamide, to open the protein structure. 0.2% trypsin was added to these pre-treated samples and incubated at 37° C. until completely digested (additional trypsin was added if required). HPLC analysis of the lysates was carried as detailed above.

The HPLC analyses showed no significant differences between the microcapsule and albumin structures. This confirms that there is significant retention of secondary and tertiary protein structure after microcapsule insolubilisation.

Coupling to FITC

FITC (fluorescein isothiocyanate) binds covalently to amino groups on the microcapsules and exemplifies the principle of derivatising charged groups, namely lysine residues, with drugs which are subsequently released by degradation of the microcapsule matrix itself.

FITC was covalently bound to three microcapsule batches. A ratio of microcapsules to FITC of 15:1 was used. 12.5 mg FITC was added to the suspended microcapsules and the mixture was incubated at 30° C. for 30 minutes. Excess fluorescein was removed by washing the microcapsules until no fluorescein was present in the washing, i.e. no leaching of the marker was observed.

The microcapsules were digested with Proteinase K at a concentration of 0.4 EU/ml. The fluorescein was released from the microcapsules as they were digested, and was measured by sampling the microcapsules suspension at various time intervals. The released FITC was separated from the microcapsules by centrifugation and quantified by measuring the absorbance at 493 nm.

The results showed that, the less heat-fixed the microcapsules, the more rapid the initial release of fluorescein. However, after 225 minutes, all samples had released greater than 90% of the fluorescein. The amount of FITC bound to the different heat-fixed microcapsules was similar, with approximately 10±0.5% mole/mole loading for all three batches.

Release rates for bound active agents can thus be adjusted by "setting" the degradation rate of the microcapsules prior to the attachment of the active agents.

Microcapsules of Example 1 were incubated with whole human blood for 30 minutes at 37° C., to determine if the microcapsules were able to stimulate platelet activation. The concentration of microparticles was equivalent to a dose of $2000 \times 10^6$ particles/kg. After 30 minutes incubation, the serum was tested for effects on platelet aggregation stimulated with collagen ADP and arachidonic acid. Effects on general hemostatic mechanisms were assessed by measurement of procoagulant activity, partial thromboplastin time; prothrombin time by appearance of fragments 1+2 and fibrinopeptide A; and fibrinolytic activity by examination of euglobulin lysis time.

At this concentration, there was no evidence of any untoward effects upon the assays tested. Thus the results suggest that the microparticles are inert and hydrophilic, unlike microparticles made by an emulsion processes.

In a further test, microparticles manufactured by the method of Example 1 were sterilised by gamma irradiation by exposure to a $Co^{60}$ source and received a dose of 25–35 Kgray. The microcapsules were reconstituted in aqueous diluent at a concentration of $1.5 \times 10^9$ microparticles/ml and administered to healthy male volunteers at doses ranging from $25-300 \times 10^6$ microparticles/kg under ethical committee approval. The microparticles were hollow and contained air which enabled their passage and persistence in the blood stream to be followed using ultrasound imaging.

Using an Acuson-128, grey scale 2D images of the right and left ventricle were acquired to monitor the circulatory life time following IV dosing. For opacification of both the left and right ventricle to occur, significant levels of microparticles must be present in the chambers. At doses from $25 \times 10^6$/kg upwards, the opacification in the right and left ventricles persisted for a period of 1 hour or more, showing that significant quantities of particles remained in the circulation.

These data show the basic microcapsule vehicle to be inert to the coaggulatory machinery in the blood, and hence ideally suited to carry therapeutics. This is completely contrary to microparticles made by emulsion processes which show rapid RES uptake and circulatory half-lives of 10 minutes or less. Furthermore, the microparticles do not require derivatisation with co-block polymers to enhance the circulatory half-life.

EXAMPLE 2

This Example shows that additives can be included in the spray-drying feedstock of the microcapsule wall-forming material, such that the resultant microcapsules can be heat-fixed at a lower temperature. Additives which allow lower cross-linking (insolubilisation) temperatures of the microcapsule polymer have utility when active drugs are co-spray-dried and hence incorporated in the matrix. By using these additives, microcapsules with heat-sensitive active agents can be insolubilised at advantageous lower temperatures.

To the spray-drying feedstock, 5 mg/ml tyrosine was added, and microcapsules were formed, using the method detailed in Example 1. No changes in the spray-drying conditions were required to obtain microcapsules.

The collected microcapsules were heat-fixed as before, but at a temperature of 100° C. for 55 minutes, significantly lower than the normal 175° C. for 55 minutes, to achieve the same cross-linking. The microcapsules produced had a mean size of 3.28±0.6 µm with 90% of the mass within 2–5 µm.

EXAMPLE 3

Example 1 details the production of 3 µm microcapsules. This Example shows that, by adjustment of the spray-drying conditions and the use of a secondary stage classification processing step, larger microcapsules may be produced with excellent control over size and size distribution. 20% HSA was spray-dried under the conditions shown in Table 3. The collected microcapsules were heat-fixed at 175° C. for 55 minutes, deagglomerated and then classified using an elbow jet classifier (see Table 4).

TABLE 3

| Spray Dryer Condition | Setting |
| --- | --- |
| Inlet Temperature | 220° C. |
| Outlet Temperature-Initial | 89.1° C. |
| Outlet Temperature-Final | 89.2° C. |
| Atomisation Pressure | 2.0 bar |
| Damper Setting | 0.5 |
| Feed Rate | 20.1 g/min |

TABLE 4

| Classification Conditions | Settings |
| --- | --- |
| Primary Air | 0.6 barg |
| Secondary Air | 2.0 barg |
| Venturi Air | 8.0 barg |

The middle classified fraction was collected and reformulated, as the classification process removes much of the excipient. The resultant free-flowing dry powder was characterised as before. The microcapsules had a mean size of 12 µm, with virtually no microcapsules below 6 µm, and 85% of the mass between 9–18 µm.

By removing particles smaller than 6 µm, systemic circulation of microcapsules, following intraarterial administration, is prevented due to capillary trapping. This has the advantage of localising the deposited drug, thereby reducing the overall amount of drug required to achieve therapeutic activity at the desired site. This is desirable, particularly in the case of cytotoxics since systemic toxicity is the major cause of detrimental side-effects.

Antibodies were then bound to the microcapsule wall surface. A FITC IgG was used to aid the detection of the bound antibody.

To 5 mg of FITC-IgG, 35 mg of sodium periodate was added. The mixture was incubated at room temperature for 1 hour, after which 20 mg microcapsules was added. The suspension was stirred for 10 minutes and then the activated antibody was bound to the microcapsules by the addition of 30 mg sodium borohydride. The reaction was allowed to proceed for 2 hours at room temperature, after which time the microcapsules were collected and washed.

A sample of the microcapsules was reduced, releasing the light chains of the bound antibodies. The microcapsules were removed and the resultant filtrate collected. The presence of FITC-labelled antibody light chains in the filtrate was measured by the use of a fluorimeter.

The linkage of antibodies to the microcapsules may also be achieved by means of tri and tetrapeptide spacers. The peptides are covalently linked to the activated sugar ring on the antibodies using the periodate and borohydride reaction detailed above. The antibodies are then linked to the microcapsules via this peptide spacer using EDCI, as detailed in Example 6.

EXAMPLE 4

This Example shows that the incorporation of additives into the spray-drying feedstock, for example HSA, will alter the chemical properties of the microcapsules produced as in Example 1, such that the number of chemical linkage sites may be greatly enhanced.

Poly-lysine was incorporated into the spray-drying feedstock at a concentration of 5 mg/ml. The spray-drying procedure was carried out as detailed in Example 1. The microcapsules produced from this modified stock had a mean size of 3.5±0.3 μm with similar physical characteristics to the HSA microcapsules such as resuspension properties.

FITC was bound to the poly-lysine microcapsules as detailed in Example 1. The microcapsules were washed until no further release of the FITC was observed. The FITC was retained bound to the HSA microcapsules, showing no release in aqueous suspension. The microcapsules were digested as detailed in Example 1 and the total amount of fluorescein bound to the microcapsules measured.

The release rate of fluorescein upon digestion showed a more rapid release than the standard microcapsules. However, a total of 20 molar % fluorescein was measured bound to the microcapsules, an increase of 50% over the standard microcapsule composition.

EXAMPLE 5

This Example shows that active agents may be linked to the shell and that their subsequent release rate is governed by degradation of the microcapsule itself.

To a 10 mg/ml solution of methotrexate, 25 mg carbodiimide (EDCI) was added. The solution was stirred for 4 hours to initiate and ensure complete activation of the methotrexate. 50 mg HSA microcapsules, produced as in Example 1, were added to the activated drug and stirred for 3 hours at room temperature. The methotrexate was chemically bound to the microcapsules via the amine groups on the albumin. The microcapsules were collected and washed to remove any loosely-bound methotrexate.

The methotrexate-linked microcapsules were characterised and also analysed for drug content. The microcapsules had a mean size of 3.2±0.6 μm with 90% by mass between 2–5 μm. The analysis of the drug content showed that the microcapsules did not release the drug when resuspended in an aqueous medium. Moreover, a three month stability trial showed no drug release after this time. Proteinase K digestion of the albumin microcapsules released the bound drug which was shown to be linked to only a limited number of amino acids and small peptides.

EXAMPLE 6

Doxorubicin was conjugated to microcapsules produced using the general method described in Example 1, with carbodiimide. 3 mg doxorubicin, 6 mg EDCI and 100 mg microcapsules were suspended in distilled water at pH 6.6 and 37° C. for 20 hr with continuous stirring and resuspension and formulated.

The doxorubicin-microcapsules were analysed for drug content and characterised. The results showed no change had occurred to the characteristics of the microcapsules during drug conjugation. Drug loading was assessed on an enzyme-digested sample of microcapsules by HPLC analysis. A loading of 2% was measured and the drug was shown to be linked only to a limited number of amino-acids or small peptides.

The activity of doxorubicin bound to polymeric carriers may prove beneficial in tumours showing the multidrug resistant phenotype.

EXAMPLE 7

In this Example, microcapsules produced using the method of Example 1 were derivatised to carry 5-fluoro-2'-deoxyuridine (FUdR). The drug was activated with succinic anhydride.

40 mg FUdR was added to 0.2M phosphate buffer at pH 8.3. To this solution, 200 mg succinic anhydride was added and the reaction mixture stirred at 30° C. for 2 hours, whilst maintaining the pH at 8.3 using 1M NaOH. The pH of the reaction mixture was adjusted to 6.5, and 0.5 g microcapsules was added. After stirring the suspension for 10 minutes, EDCI and N-hydroxysuccinimide in a ratio of 15:1 were added, and the coupling reaction was allowed to proceed at room temperature. After 24 hours, the microcapsules were collected and washed, and the presence of FUdR on the microcapsules was confirmed by HPLC analysis.

Acid hydrolysis of the drug-linked microcapsules was carried out in an ASTED system using 1% TFA, and the subsequent release of the FUdR was monitored at 269 nm. 15% w/w FUdR was found to be bound to the microcapsules via the acid-hydrolysable linkage.

Cytotoxic Activity

Cytotoxic activity of the drug-microcapsule conjugates of Examples 5 to 7 was measured in vitro. The HSN cell line was used. This is a chemically-induced rat colonic sarcoma, which produces liver tumours in an animal model with a vascular pattern similar to that seen in human colorectal liver metastases. Cell kill was measured indirectly using MTT. This is reduced in active mitochondria to formazan, a coloured metabolite. HSN cells were incubated in multi-well plates to which was added a control dose of drug or drug-microcapsule lysate. After a range of exposure times, MTT was added to the wells and the concentration of formazan measured as an indication of cell death. The assay was calibrated for this cell line against a range of known cell numbers.

All three drugs (methotrexate, FUdR and doxorubicin) had similar dose response curves for the native drugs and the drug-microcapsules lysate, indicating that cytotoxic activity was similar. The maximum reduction in cell activity for all three drugs and lysates was approximately 80%. For FUdR and methotrexate, the steepest part of the dose response curve was from 1 μg/ml down to 0.01 μg/ml and for doxorubicin from 0.1 μg/ml, well within serum ranges seen in vivo. Control lysates of underivatised microcapsules showed no cytotoxic activity.

The following experiment compares doxorubicin as the free drug and doxorubicin microcapsules in the MCF7 cell line and the related doxorubicin-resistant cell line MCF7/dox. It was noted that the doxorubicin-resistant cell line had a lower $IC_{50}$ with microcapsules compared with free drug, i.e. the microcapsule presentation reversed the drug resistance.

More specifically, the experiment compared the cytotoxicity of a novel preparation of doxorubicin covalently-linked to a human serum albumin microsphere carrier between 2 and 3 µm in diameter on a doxorubicin-sensitive human breast cancer cell line and its doxorubicin-resistant P-glycoprotein expressing daughter cell line. Human serum albumin microspheres (HSAMS) were produced and heat-stabilised prior to incubation with 1-(3-dimethylaminopropyl)-3-ethylcarbodmiimide (EDC) and doxorubicin (Dox). The EDC "activates" exposed carboxyl residues on the HSAMS, allowing covalent binding of Dox amino sugar. The human MCF7 cell line and its doxorubicin-resistant daughter cell line, MCF7/Dox were used.

Cells were plated in 24 well plates at a concentration of 50,000 cells/well and incubated with either doxorubicin or a solution of doxorubicin-HSAMS at varying concentrations for 24 hours. The medium was then changed, cells were incubated for a further 72 hours before harvesting and counting with a Coulter Counter. The $IC_{50}$ for the MCF7 parent cell line with doxorubicin was 0.031 µg/ml (Standard error (SE)=0.002) whereas for the doxorubicin-resistant line it was 0.387 µg/ml (SE=0.049, p=0.002). 24 hour incubation of the doxorubicin-resistant cell line with the drug-loaded microspheres showed an $IC_{50}$ of 0.062 µg/ml (SE=0.037) (expressed as µg doxorubicin per ml), which was significantly lower than the $IC_{50}$ for doxorubicin in this cell line (p=0.006) and not significantly different from that seen in the parent cell line (p=0.45).

EXAMPLE 8

This Example illustrates linkage of active compound, not directly to the microcapsule shell wall but via a degradable spacer or linker. This enables greater control of both the linking and release of the active compound.

Using the technology detailed in WO-A-9317713 for linking drugs to soluble carriers, naproxen has been linked to microcapsules using a lactic acid spacer. To a 10 mmol suspension of L-lactic acid in dimethylformamide, 20 mmol triethylamine and 10 mmol pentamethylbenzyl (PMB) chloride were added. The mixture was heated until a solution was formed and then held at room temperature. Excess sodium carbonate was added after incubation of the solution overnight, and the precipitated ester, L-lactic acid-PMB, was collected, washed and dried.

To a solution containing 10 nmol naproxen, L-lactic acid-PMB and 4-dimethylaminopyridine, a 11 mmol solution of dicyclohexylcarbodiimide was added. The reaction mixture was stirred at 25° C. and the formation of the naproxen linker monitored. On completion of the reaction, the naproxen-L-lactic acid linker was collected, washed and dried.

The PMB protecting group was removed by the reaction of the naproxen linker with anisole and trifluoroacetic acid at room temperature for 2 minutes. Excess reagent was removed under vacuum and the residue was collected and washed. Acidification of the washed residue produced naproxen-L-lactic acid, which was extracted, washed and dried under vacuum at 50° C.

The naproxen-L-lactic acid was activated by its 1:1 reaction with carbodiimide, followed by the addition of 1 mmol N-hydroxysuccinimide. The active naproxen-L-lactic acid-NHS was added to HSA microcapsules at a 5:1 ratio in a borate buffer. The resultant product was collected and dried.

The dried naproxen microcapsules were formulated, resulting in a free-flowing powder, with a microcapsule mean size of 3.5±0.6 µm. 90% of the mass of the microcapsules was between 2 and 5 µm.

Analysis of the product was carried out using Capillary Zonal Electrophoresis (Beckman, UK). This showed the presence of the drug on the microcapsules. The release of the drug using esterases and subsequent analysis of the released naproxen were carried out using an ASTED system linked to a Gilson HPLC (Anachem UK). The drug was shown to be intact and in its native form.

EXAMPLE 9

The spray-drying production of the microcapsules allows control over many facets of the process and final characteristics of the microcapsules. The surface characteristics of the final microcapsules can be altered such that ligands for enzymes or receptors may be incorporated into the microcapsule shell. In this Example, the number of arginine residues is increased, and this enhancement was used to bind TPA.

Using the method of Examples 1 and 5, poly-arginine was added to the spray-drying feedstock. Using the same conditions as described in Example 1, microcapsules are produced. The microcapsules have a mean size of 3.31±0.6 µm and 90% of the mass is between 2–5 µm.

To 100 mg of microcapsules, a solution containing 250 µg TPA is added. The suspension is agitated for 2 hours after which the microcapsules are removed and briefly washed. The concentration of TPA remaining in the reaction solution is measured by RP-HPLC having reduced the peptide by incubation in 20 mM DTT at 37° C. for 30 min in the presence of 8 M urea. The analysis of the fragments is carried out using a gradient of 10–40% acetonitrile-water and 0.1% TFA over 60 minutes.

The TPA-microcapsules are analysed for the presence of TPA using the clot lysis assay. A fibrin clot is produced by combining fibrinogen, thrombin and the TPA microcapsules. Plasminogen is then added to the clot and a glass bead added to the surface to allow the assay end point, i.e. clot lysis, to be determined. The fall of the glass bead through the lysed clot shows that the TPA is both bound to the microcapsules and that it is still active.

In addition, the amount of TPA bound to the microcapsules is determined by using a modified fibrin assay. To a microtiter plate well, a thin agarose gel containing fibrinogen and thrombin is added. To the gel, 20 µl suspension of TPA-microcapsules and plasminogen are added. After 30 minutes, the plate is washed and the reduction in the gel turbidity is determined using a microtiter plate reader at 340 nm. The concentration of TPA present on the microcapsule is determined using appropriate TPA standards. The results show that between 15 and 20% TPA is bound to the microcapsules.

The TPA microcapsules can have utility as a deposit thrombolytic agent for administration at the time of angiography, similar to that proposed in WO-A-9408627 as a deposit echocontrast agent, the advantage being maintenance of a localised reservoir of TPA in the myocardium.

What we claim is:

1. A sterile powder comprising smooth, spherical microparticles of 0.1 to 50 µm in diameter, wherein said microparticles comprise a cross-linked material selected from the group consisting of an amino acid, a polyamino-acid and a polypeptide, the microparticles being hydrophilic and capable of reconstitution in water to give a monodisperse suspension, and wherein said sterile powder additionally comprises a physiologically or diagnostically-active component linked directly or indirectly to the microparticles via free functional groups thereon.

2. A powder according to claim 1, produced by a process comprising the steps of (i) spray-drying a water-soluble and cross-linkable material selected from the group consisting of an amino acid a polyamino acid and a polypeptide, said material having free functional groups thereon, (ii) cross-linking said material such that said groups are retained in free form, and (iii) linking a physiologically or diagnostically-active component to the cross-linked material via said groups.

3. A powder according to claim 1, which comprises an additional water-soluble material that facilitates enzymatic biodegradation.

4. A powder according to claim 1, wherein the active component is a drug, chemical spacer, a ligand for an enzyme or receptor, or an antibody.

5. A powder according to claim 4, wherein the active component is a cytotoxic agent.

6. A powder according to claim 5, wherein the microparticles additionally comprise a targeting agent.

7. A powder according to claim 4, wherein the active component is selected from the group consisting of fibrinogen and thrombin.

8. A method of wound therapy or surgical repair, which comprises administering to the wound or surgical locus an effective amount of the powder of claim 7.

9. A powder according to claim 2, wherein step (i) comprises spray-drying a solution of the water-soluble material, and step (ii) comprises cross-linking the spray-dried material with heat and in the presence of less than 4% moisture.

10. A powder according to claim 1, wherein said free functional groups are selected from the group consisting of amine, hydroxyl, carboxyl and sulfhydryl.

11. A powder according to claim 10, wherein said free functional groups are selected from the group consisting of amine, hydroxyl and carboxyl.

12. A powder according to claim 1, wherein the microparticles have a ratio of interquartile range to mean diameter of 0.2 to 0.5.

13. A powder according to claim 12, wherein 95% of the microparticles are smaller than 6 $\mu$m, and 80% of the microparticles are in the range of 1 to 6 $\mu$m.

14. A powder according to claim 12, wherein 90% of the microparticles are smaller than 20 $\mu$m, and less than 5% of the microparticles by volume are smaller than 6 $\mu$m.

15. A suspension of microparticles as defined in claim 1, suitable for parenteral administration.

16. A suspension according to claim 15, wherein the microparticles comprise free functional groups selected from the group consisting of amine, hydroxyl, carboxyl and sulfhydryl said suspension suitable for intravenous administration.

17. A suspension comprising the powder of claim 12, wherein the microparticles comprise free functional groups selected from the group consisting of an amine, hydroxyl, and carboxyl, said suspension suitable for intraarterial administration.

18. A method for the treatment of multi-drug resistance in a patient exhibiting a tumor, which comprises administering to the patient an effective amount of the powder of claim 5 or claim 6.

* * * * *